(12) United States Patent
Huner et al.

(10) Patent No.: US 6,787,147 B1
(45) Date of Patent: Sep. 7, 2004

(54) SOLAR RADIATION PROTECTION COMPOSITION

(76) Inventors: Norman Huner, 207 Windsor Ave., London (CA), N6C 2A5; Mariana Krol, 380 Fox Ave., London (CA), N6G 1H6; Alexander Ivanov, 100-40 Summit Ave., London (CA), N6H 4S3; Fathey Sarhan, 3277 Achim St., Laurent (CA), H4K 1V5

( * ) Notice: Subject to any disclaimer, the term of this patent is extended or adjusted under 35 U.S.C. 154(b) by 0 days.

(21) Appl. No.: 09/830,193

(22) PCT Filed: Oct. 22, 1999

(86) PCT No.: PCT/CA99/00981

§ 371 (c)(1),
(2), (4) Date: Jan. 16, 2002

(87) PCT Pub. No.: WO00/24369

PCT Pub. Date: May 4, 2000

(30) Foreign Application Priority Data

Oct. 23, 1998 (CA) ............................................. 2251457

(51) Int. Cl.$^7$ ............................ A61K 7/00; A61K 7/42; A61K 7/44
(52) U.S. Cl. ........................... 424/401; 424/59; 424/60; 424/400
(58) Field of Search ................................ 424/400, 401, 424/59, 60

(56) References Cited

U.S. PATENT DOCUMENTS

| | | | |
|---|---|---|---|
| 3,920,834 A | * | 11/1975 | Klaui et al. ................... 424/59 |
| 5,508,026 A | * | 4/1996 | Gerwick et al. ............... 424/59 |
| 5,691,158 A | | 11/1997 | Reece et al. |

FOREIGN PATENT DOCUMENTS

| | | |
|---|---|---|
| EP | 0 748 625 A1 | 12/1996 |
| FR | 2.100.886 | 7/1971 |
| FR | 2 100 886 A | 3/1972 |
| FR | 2.430.765 | 7/1978 |
| FR | 2 430 765 A | 2/1980 |
| FR | 2.722.094 | 7/1994 |
| FR | 2 722 094 A | 1/1996 |
| JP | 03 118312 A2 | 5/1991 |
| JP | 05 163143 A | 6/1993 |
| JP | 08 143418 A | 6/1996 |
| WO | WO 93/20183 | 10/1993 |
| WO | WO 97/47278 | 12/1997 |
| WO | WO 99/48468 | 9/1999 |

OTHER PUBLICATIONS

STN, File Supplier, Karlsruhe, DE, File Chemical Abstracts, vol. 115, AN=214553 XP002127818 see the abstract.
STN, File Supplier, Karlsruhe, DE, File Chemical Abstracts, vol. 13, AN=84603 XP002127819 see the abstract.
Database WPI Week 199632 Derwent Publications Ltd., London, GB; AN 1996–318814 XP002127820 & JP 08 143418 A (Owa Kasei KK) abstract.
Xiong, Fusheng et al. "Assessment of UV–B sensitivity of photosynthetic apparatus among microalgae: short–term laboratory screening versus long–term outdoor exposure." J. Plant Physiol., 1999, vol. 155, pp 54–62.
Ivanov, Alexander G. et al. "Protection of Photosystem II against UV–A and UV–B radiation in the cyanobacterium *Plectonema boryanum*: The role of growth temperature and growth irridance." Photochemistry and Photobiology, 2000, vol. 72, No. 6, pp 772–779.
Black, Homer S. "Antioxidants and carotenoids as potential photoprotectants." Cosmet. Sci. Technol. Ser., 1990, vol. 10, pp. 267–278.
Miskiewicz, E.I. et al. "Does myxoxanthophyll have a photoprotective function in the cells of the cyanobacterium *Placonema boryanum* UTEX 485?" The 1999 Annual Meeting of the American Society of Plant Physiologists, Abstract and Poster Presentation, Baltimore, Jul. 24–28, 1999.
PCT Search, Report dated Jan. 18, 2000 for PCT/CA99/00981.
Ferran Garcia–Pichel and Richard W. Castenholz, Occurrence of UV–Absorbing, Mycosporine–Like Compounds among Cyanobacterial Isolates and an Estimate of Their Screening Capacity, Applied and Environmental Microbiology, Jan. 1993, p. 163–169.

* cited by examiner

*Primary Examiner*—Shelley A. Dodson
(74) *Attorney, Agent, or Firm*—McKee, Voorhees & Sease, P.L.C.

(57) ABSTRACT

The invention relates to sunscreen compositions for humans including naturally occurring sunscreen agents from plants, algae, cyanobacteria, fungi and bacteria that protect against exposure to solar radiation. The active sunscreen agents are compounds that naturally occur in plants, algae, cyanobacteria, fungi and bacteria and derivatives of these compounds.

26 Claims, 7 Drawing Sheets

SOLAR RADIATION PROTECTION COMPOSITION

FIELD OF THE INVENTION

The invention relates to novel compositions that protect humans and objects from damaging exposure to solar radiation. The invention also relates to active compounds which occur naturally in plants, algae and cyanobacteria as well as to the chemical derivatives of these compounds that protect against solar radiation.

BACKGROUND OF THE INVENTION

The various layers of the earth's atmosphere absorb most of the solar radiation reaching earth with the more energetic ultraviolet radiation (UV) filtered out by the ozone layer. Of the solar radiation reaching the earth's surface that is of biological interest, only about 2% of the radiation is UV-B with its characteristic wavelength range of 280 to 315 nm. The remainder consists mainly of UV-A with the characteristic wavelength range of 315 to 400 nm, visible light of 400 to 700 nm and infrared radiation (>740 nm). Anthropogenic depletion of the stratospheric ozone layer (Madronich et al., 1995, Ambio 24: 143) has resulted in elevated levels of UV radiation reaching the earth and these levels are expected to increase In the future. The higher levels of radiation have been linked to a significant rise in the incidence of skin lesions and skin cancer in humans (Jagger, 1985, Solar-UV Actions on Living Cells, Praeger Pub., N.Y.). Skin cancer now occurs more frequently than all other cancers combined. In 1998, there will be approximately one million new cases of skin cancer in North America alone. According to the American Cancer Society, diagnosed cases of skin cancer have increased at a rate of about 4% per year in the U.S. since 1973 (Science News 1997, 151: 383). Thus, increased incidence of skin cancer has become a serious health concern.

Skin damage is caused by both UV-A and UV-B radiation. Although damage caused by UV-B radiation has been extensively studied (Motoyoshi et al., 1998, Cosmetics and Toiletries 113: 51), only a few published papers describe the effects of UV-radiation on human hair or quantify photodamage (Hoting et al., 1995, J. Soc. Cosm. Chem. 46: 85). Erythma is the most apparent result of the sunburn reaction but sunburn can also disturb DNA and RNA structure and metabolism. The most serious results of chronic sun exposure are photoaging and photocarcinogenesis.

The natural human skin pigment, melanin, has evolved to provide a certain level of protection against the damaging effects of solar radiation (Kollias et al., 1991, J. Photochem. Photobiol. B: Biol. 9:135). The epidermis has the ability to interfere with the transmission of UV-radiation. Only about 20% of the incident radiation between 300 and 350 nm reaches the dermis. This penetration rises gradually to about 80% at or near 550 nm. Evidently, the cells of the stratum comeum are a remarkably effective block against UV-B radiation. Keratinocytes are, however, exposed to UV-A radiation even though the more energetic UV-B wavelengths are excluded. Moreover, UV-A radiation has been shown to induce mutations and to be potentially lethal (Jagger, 1985, Solar-UV Actions on Living Cells, Praeger Pub., N.Y.).

Strategies to protect skin against solar radiation have most often involved the application of compositions that either block the radiation or absorb the harmful UV component (Gasparro et al., 1998, Photochem. Photobiol. 68:243). Although sunscreens on the market today protect people from sunburn to varying degrees, they do not prevent skin cancer. The use of sunscreens has increased significantly in the last five to ten years but cases of melanoma have also continued to rise (ASP News, 1998, 27:7). Typical sunscreen preparations block UV-B but UV-A passes through very easily. It has been reported that although UV-B causes sunburn, UV-A plays a major role in inducing skin cancer (ASP News, 1998, 27:7). We believe that there is a clear need to devise strategies to supplement the body's natural protective mechanisms against both UV-A and UV-B radiation. A suitable composition must have high activity against UV-A as well as UV-B, be safe for application to human skin and provide good cosmetic application and appearance.

Cosmetic chemists have incorporated sunscreen activities into formulations in order to achieve the desired protection. Formulating products with an improved UV screening capacity is a challenge for cosmetic chemists due to concerns over the use of high levels of organic actives (Dromgoole et al., 1990, Sunscreens: development, evaluation and regulatory aspects. Marcel Dekker, N.Y., pp 313–317). Sunscreen compounds are most effective when they remain on the surface of the epidermis but unfortunately, they are often absorbed to deeper layers of the skin, thereby limiting their efficacy and causing irritation. Cosmetic chemists use organic compounds in their sunscreen formulations. For example, combinations of nylon, butyl methoxydibenzoylmetan and octylmethoxycinnamate have been used as UV-screens in many solar lotions. (Cosmetics and Toiletries, 1998, 113: 83; Gasparro et al., 1998, Photochem. Photobiol. 68:243) (see Table 1).

TABLE 1

Example of a Sunscreen Lotion/Cream Formulation (Cosmetics & Toiletries, 1998, 113:84)

| | | % Composition |
|---|---|---|
| A. | Carbomer | 0.15 |
| B. | Water | 70.70 |
| C. | Propylene glycol | 2.0 |
| | methylparaben | 0.20 |
| D. | Sodium cocoyl lactylate | 0.50 |
| | Octoaryl alcohol | 1.60 |
| | Octyl methoxycinnamate | 7.00 |
| | Benzophenone-3 | 2.00 |
| | Octyl salicylate | 3.50 |
| | C12-15 alkyl benzoate | 5.00 |
| | Isopropyl palmitate | 2.00 |
| | Propylparaben | 1.10 |
| E. | DMDM hydantoin | 0.20 |

This formulation provides some protection against UV-B but provides minimal protection against UV-A.

Based on recent reports showing the harmful effect of UV-A exposure on skin tissue, it is imperative that the cosmetic industry develops as soon as possible protective lotions by broadening the light absorption range of skin lotions (Gasparro et al., 1998, Photochem. Photobiol. 68:243).

Photoautotrophic plants and microorganisms such as green algae and cyanobacteria have evolved to protect the sensitive photosynthetic process against the damaging effects of UV-radiation. Photosynthetic organisms as well as heterotrophic organisms such as fungi and bacteria produce naturally occurring compounds that protect them from the damaging effects of solar radiation. To date, these organisms have not been exploited as sources for sunscreen compounds that can be applied to human skin. This is probably due in part, to the scientific background of the industrial scientists involved in the cosmetic industry. These scientists are typically synthetic organic chemists with limited knowledge and expertise in photosynthesis research and the biology and biochemistry of terrestrial plants, green algae and cyanobacteria. It would be helpful if the naturally occurring sunscreens from these organisms could be adapted to protect humans from solar radiation.

SUMMARY OF THE INVENTION

We identified several naturally occurring compounds which: (1) act as natural sunscreening agents; (2) protect not only against visible light and UV-B radiation but also protect against UV-A radiation; (3) can be produced in large quantities; (4) are easily isolated; (5) are easily incorporated in sunscreen lotions which will offer protection to humans against both harmful forms of ultraviolet radiation (UV-A and UV-B); (6) and as a consequence, should reduce the development of skin cancers, sunburn, photoaging and photodamage to hair and eyes upon exposure to sunlight.

The invention includes several main components: First, we showed that cyanobacteria principally use a combination of three different types of compounds to protect themselves from the harmful affects of solar radiation: (i) carotenoids (ii) scytonemin and (iii) mycosporine amino acids. These compounds may be used to formulate sunscreen compositions that provide significant protection from solar radiation. The compositions are non-toxic, resistant to absorption by the skin, non-irritating to the skin and capable of application to the skin in compositions that create a uniform, continuous film. In addition, the compounds are chemically stable and resistant to chemical and photodegradation when on the skin. The formulations will not only protect human skin from photoaging and photodamage but also will provide protection to human hair and other surfaces. In addition, these compounds can be integrated into or coated on objects such as windows, contact lenses, sunglasses, paints and films for protection against the damaging effects of prolonged exposure to solar radiation. The invention also relates to a method of protecting human skin and other surfaces against the deleterious effects of solar radiation by topically applying thereto an effective amount of a composition of the invention.

Second, we have shown a novel method to induce overproduction of these natural screening compounds. For example, these compounds are very easy to produce in cyanobacteria. Cyanobacteria are amenable to manipulation by controlling culturing conditions. Since these compounds are produced naturally by photosynthetic organisms, the formulations are "eco-friendly" and can be extracted from organisms easily and efficiently. The compounds may also be chemically synthesized.

Next, based on the results of research described above, we developed a sensitive, relevant biological assay to test the potential of various screening compounds to protect against UV-radiation. This is accomplished by exploiting the sensitivity of cyanobacterial photosystems to UV-radiation.

Finally, we identify useful naturally occurring sunscreen compounds from other organisms and methods for their isolation and use.

The sunscreen agents, in particular those from cyanobacteria, provide a synergistic effect. Compositions containing the three compounds isolated from cyanobacteria with a carrier are superior to those which may be obtained, with an equal amount of sunscreen compound and a carrier identical in nature, employing either of the compounds alone. The three compounds are preferably present in the final composition in relative proportions chosen so that the synergistic effect, at the level of the sun protection factor conferred by the resulting composition, is optimal.

In one embodiment, the invention is a sunscreen composition including a carotenoid or a carotenoid derivative and a carrier. In an alternate embodiment, the invention is a sunscreen composition including a polyphenolic compound or a polyphenolic compound derivative and a carrier. In another embodiment, the invention is a sunscreen composition comprising a mycosporine amino acid or a mycosporine amino acid derivative and a carrier. In yet another embodiment, the invention is a sunscreen composition comprising a carotenoid or a carotenoid derivative, a polyphenolic compound or a polyphenolic compound derivative, a mycosporine amino acid or a mycosporine amino acid derivative and a carrier. The compositions protect skin, hair and other surfaces from solar radiation. The carriers are compatible (cosmetically and otherwise) with the surface to which the compositions to which they will be applied, for example, human skin or hair. The carriers are preferably at least one of either water, a gas, a water-based liquid, an oil, a gel, an emulsion, a dispersion or a mixture thereof.

The carotenoid preferably comprises a cyanobacterial carotenoid, such as a compound selected from the group consisting of β-carotene, lutein, neoxanthin, zeaxanthin, violaxanthin, caloxanthin, nostoxanthin, echinenone, canthexanthin, oscillaxanthin and myxoxanthophyll. The polyphenolic compound is preferably a cyanobacterial polyphenolic compound such as scytonemin. The mycosporine amino acid is preferably a compound selected from the group consisting of mycosporinelycine, palythine, asterina-330, palythinol, palythene, porphyra-334, mycosporineglycine:valine and shinorine. The carotenoid is preferably present in an amount of about 2 mg by weight. The polyphenolic compound is preferably present in an amount of about 1 mg by weight. The mycosporine amino acid is preferably present in an amount of about 1 mg by weight.

Suitable compositions include an oil-in-water emulsion or a water-in-oil emulsion. In a variation, the sunscreen composition further includes at least one cosmetically acceptable adjuvant or additive, such as a preservative, organic solvent, browning agent, antioxidant, stabilizer, emollient, silicone, alpha-hydroxy acid, demulcent, anti-foaming agent, moisturizing agent, vitamin, fragrance, ionic or nonionic thickener, surfactant, filler, thickener, sequestrant, polymer, propellant, alkalinizing or acidifying agent, opacifier, fatty compound or colorant.

Other useful compositions are a nonionic vesicle dispersion, emulsion, cream, milk, gel, ointment, suspension, dispersion, powder, solid stick, foam or spray. The composition may also include a makeup or an anhydrous or aqueous solid or paste. The composition may also include a hair rinse, spray, mist, gel, mousse, shampoo, conditioner, lotion, emulsion and colouring product.

In another embodiment, the invention relates to a method of protecting human skin human hair or another surface from solar radiation, by topically applying thereto an effective amount of the compositions of the invention.

An alternate embodiment of the invention is a sunscreen composition including a photoautotrophic cell extract and a carrier. Carriers are compatible (cosmetically and otherwise) with the surface to which the compositions to which they will be applied, for example, human skin or hair. The carriers are preferably at least one of either water, a gas, a water-based liquid, an oil, a gel, an emulsion, a dispersion or a mixture thereof. The extract is preferably present in an amount of about 0.1 to 25% by weight or about 0.1 to 10% by weight. The sunscreen composition including a photoautotrophic cell extract and a carrier, wherein the photoautotrophic cell extract is preferably obtained by extraction of photoautotrophic cells with methanol and acetone.

In another embodiment, the invention is a kit for assaying a test compound to determine its sunscreen efficacy, comprising: a photoautotrophic cell culture, a chlorophyll fluorometer and an artificial filter for containing the test compound. The invention also includes a method for protecting the human skin, human hair or another surface from solar radiation, comprising topically applying thereto an effective amount of the sunscreen composition of the invention. The invention also includes a method of inducing cyanobacteria to produce myxoxanthophyll, scytonemin and/or mycosporine amino acid, the method comprising culturing the cyanobacteria under conditions of high excitation pressure. The invention also includes a method of producing an extract having an increased concentration of at least one of myxoxanthophyll, scytonemin and/or mycosporine amino acid, the method preferably including: culturing cyanobacteria under conditions of high excitation pressure and isolating an extract including at least one of myxoxanthophyll, scytonemin and mycosporine amino acid. In the methods the conditions of high excitation pressure are preferably about 5° C. and a light intensity of about 150 $\mu$mol m$^{-2}$ s$^{-1}$ or about 29° C. and a light intensity of about 750 $\mu$mol m$^{-2}$ s$^{-1}$. The methods preferably further comprising isolating at least one of myxoxanthophyll, scytonemin and/or mycosporine amino acid. The invention also includes a method of assaying a compound to determine its sunscreen efficacy, including extracting photoautotrophic cells to produce a solution; producing an artificial filter; determining whether the artificial filter protects photosystem II photochemical efficiency from UV radiation. The protection of photosystem II photochemical efficiency from UV radiation is determined by measuring chlorophyll a fluorescence.

The invention also includes method for protecting human eyes from solar radiation, comprising applying at least one of a carotenoid, a polyphenolic compound and/or a mycosporine amino acid or a derivative of a carotenoid, a polyphenolic compound or a mycosporine amino acid to an eye wear lens or a window.

In another embodiment, the sunscreen composition includes a light absorbing amino acid or a light absorbing amino acid derivative and a carrier.

The invention also includes a sunscreen composition comprising: a carotenoid or a carotenoid derivative, a polyphenolic compound or a polyphenolic compound derivative, a light absorbing amino acid or a light absorbing amino acid derivative and a carrier. The amino acid or amino acid derivative is preferably selected from the group consisting of tyrosine, tryptophan, a tyrosine derivative and a tryptophan derivative. The derivatives have sunscreen activity which means that they are capable of absorbing light (preferably ultraviolet radiation) and are useful in the sunscreen compositions of the invention to reduce damage caused by light.

The invention relates to a sunscreen composition comprising a carrier and at least one compound selected from the group consisting of: a carotenoid, a carotenoid derivative having sunscreen activity, a polyphenolic compound, a polyphenolic compound derivative having sunscreen activity, sunscreen amino acid and a sunscreen amino acid derivative. Another aspect of the invention relates to a sunscreen composition including: a) a carotenoid or a carotenoid derivative having sunscreen activity; b) a polyphenolic compound or a polyphenolic compound derivative having sunscreen activity; and c) a light absorbing amino acid having sunscreen activity and a light absorbing amino acid derivative having sunscreen activity. The amino acid or amino acid derivative may be one of tyrosine, tryptophan, a tyrosine derivative having sunscreen activity and a tryptophan derivative having sunscreen activity.

The invention also includes a method of reducing degradation of a chemical that is sensitive to ultraviolet light comprising applying a composition of the invention to the chemical. The chemical is a herbicide, a pesticide, an auxin, a gibberellin, abscisic acid, a cytokinin, derivative of a carotenoid, a polyphenolic compound, a mycosporine amino acid and or a derivative of any of the foregoing (mixtures or pure preparations).

The invention also includes a method of determining the sunscreen activity of an extract, including: extracting photoautotrophic cells to produce a solution; producing an aqueous filter, determining whether the aqueous filter protects photosystem I or II from UV radiation wherein improved protection from UV radiation indicates that the compound has sunscreen activity. Compounds may also be purified from the extracts for use in the method.

The invention includes a system for determining the sunscreen activity of a test compound including:
  a) light means or light member for generating ultraviolet radiation;
  b) container means or container member, coupled to the light means, for containing a photoautotrophic bacterial culture, homogenate or extract thereof having PSI or PSII activity;
  c) sample means or sample member for holding a test compound, interposed between the light means and the container means.

The system may further include a scoring means or a scoring member for assaying the culture, homogenate or extract to determine PSI or PSII activity, wherein the amount of decrease in PSI or PSII activity caused by ultraviolet radiation indicates the sunscreen activity of the test compound.

The invention also includes a method for determining the sunscreen activity of a test compound comprising the steps of:
  (a) generating ultraviolet radiation for passing through the test compound;
  (b) exposing a photoautotrophic bacterial culture, homogenate or extract thereof having PSII activity to the ultraviolet radiation being passed through the test compound, the test compound being spaced from the culture, homogenate or extract;
  (d) assaying the culture, homogenate or extract for PSI or PSII activity; and
  (e) correlating the PSI or PSII activity to the sunscreen activity of the test compound. Purified compounds (synthetic or isolated from culture, homogenate or extract), photoautotrophic bacterial culture, homogenate or extract may be tested in the systems or methods of the invention.

The method may further include determining the sun protection factor of the test compound.

The invention also includes a method for reducing ultraviolet light damage to a surface, including applying to the surface an effective amount of an extract from a photoautotroph, wherein the extract has sunscreen activity.

The photoautotroph may be selected from the group consisting of photoautrotrophic bacteria, photoautrotrophic plants, photoautotrophic fungi or heteroautotrophic bacteria. The surface may be skin (eg human skin). In the method, the extract includes at least one compound from the group consisting of: a carotenoid, a carotenoid derivative having light absorption activity, a polyphenolic compound, a polyphenolic compound derivative having light absorption activity, a light absorbing amino acid and a light absorbing amino acid derivative.

BRIEF DESCRIPTION OF THE DRAWINGS

Preferred embodiments of the invention will be described in relation to the drawings in which.

DETAILED DESCRIPTION OF THE INVENTION

Preferred embodiments of the invention will be described in relation to the data from our photosynthetic experiments.

Light is a fundamental form of energy that enters our biosphere through the process of photosynthesis and ultimately sustains all living organisms. In photosynthetic organisms, this light energy is absorbed by pigments such as chlorophyll which are present in essential structures called photosystems. With the help of photosystem I and photosystem II , the solar radiation absorbed by the pigments is subsequently converted to chemical energy that is used to make complex sugars from relatively simple carbon dioxide molecules present in our air. Photosynthetic organisms face an important conundrum: although they require light for photosynthesis and, thus, require light to survive, exposure to excessive solar radiation containing UV-A and UV-B can destroy the photosystems. Thus, it is imperative that plants, green algae and cyanobacteria protect these photosystems from damaging UV radiation.

Identification of Sunscreen Compounds

Figure 1:
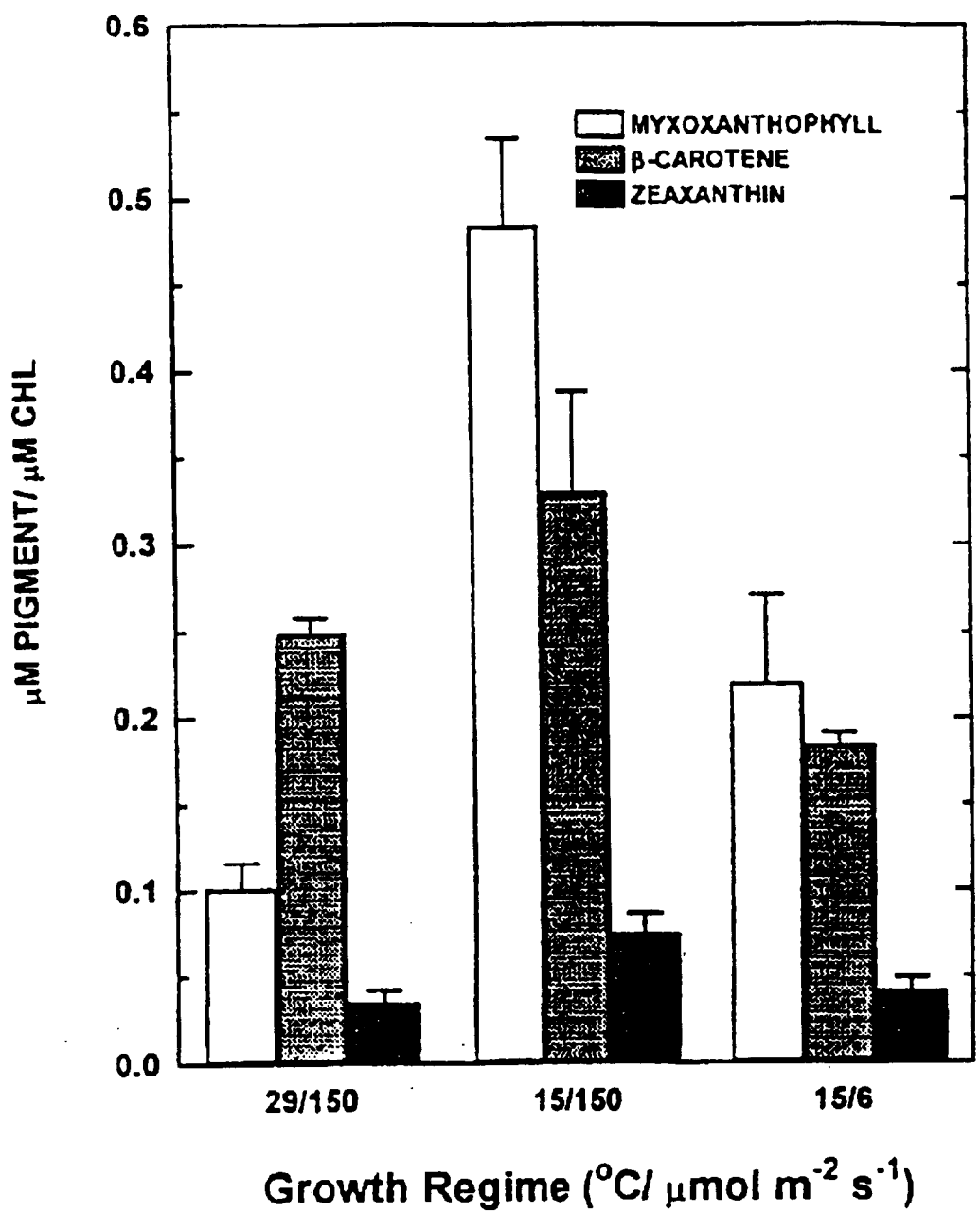
FIG. 1. Effects of exposure to excessive radiation on the carotenoid composition of Plectonema boryanum. Conditions of excessive radiation (15/150) were created by exposing cell cultures to low temperature (15° C.) and moderate light intensity (150 $\mu$mol m$^{-2}$ s$^{-1}$). Control cultures (29/150) were exposed to high temperature (29° C.) and moderate light intensity (150 $\mu$mol m$^{-2}$ s$^{-1}$). Cell cultures relieved from exposure to excessive radiation (15/6) were exposed to low temperature (15° C.) but low light intensity (6 $\mu$mol m$^{-2}$ s$^{-1}$). Mean values±were calculated from 7 to 9 measurements from 3 to 5 independent experiments.

We have shown that when the cyanobacterium, Plectonema boryanum, is exposed to conditions whereby the photosystems are exposed to too much light energy, the cultures increase their production of three important sun-screening agents: the carotenoid, myxoxanthophyll and scytonemin and mycosporine amino acids. When this cyanobacterium is exposed to excessive radiation (FIG. 1, 15/150), this organism produces about 5 times more myxoxanthophyll compared to control, untreated cells (FIG. 1, 29/150). This response appears to be specific for myxoxanthophyll since the other major carotenoids, $\beta$-carotene and zeaxanthin, exhibit minimal increases. Furthermore, when these cells were relieved from exposure to excessive radiation (FIG. 1, 15/6), the levels of myxoxanthophyll decreased to levels close to that of controls (FIG. 1: compare 15/6 with 29/150). In addition to the accumulation of the carotenoid myxoxanthophyll, these cells (Table 2, 15/150) doubled the levels of the UV-absorbing compounds scytonemin (Scy) and mycosporine amino acids (MM) relative to control, untreated cells (Table 2, 29/150). As observed with myxoxanthophyll, the levels of scytonemin and mycosporine returned to levels found in controls when the cells were relieved from exposure to excessive radiation (Table 2, compare 15/6 with 29/150).

TABLE 2

Effects of growth regime (temperature and light (photosynthetic photon flux density) on the content of UV-absorbing compounds scytonemin (Scy) and mycorsporine amino acids (MAA). Mean values ±SE are calculated from 3 independent experiments.

| Growth Regime (° C., mol photons m$^{-2}$s$^{-1}$) | mg Scy/mg chlorophyll | mg MAA/mg chlorophyll |
| --- | --- | --- |
| 29/150 | 0.687 ± 0.010 | 3.843 ± 0.125 |
| 15/150 | 1.145 ± 0.090 | 8.450 ± 0.213 |
| 15/6 | 0.724 ± 0.010 | 4.969 ± 0.270 |

Figure 2:
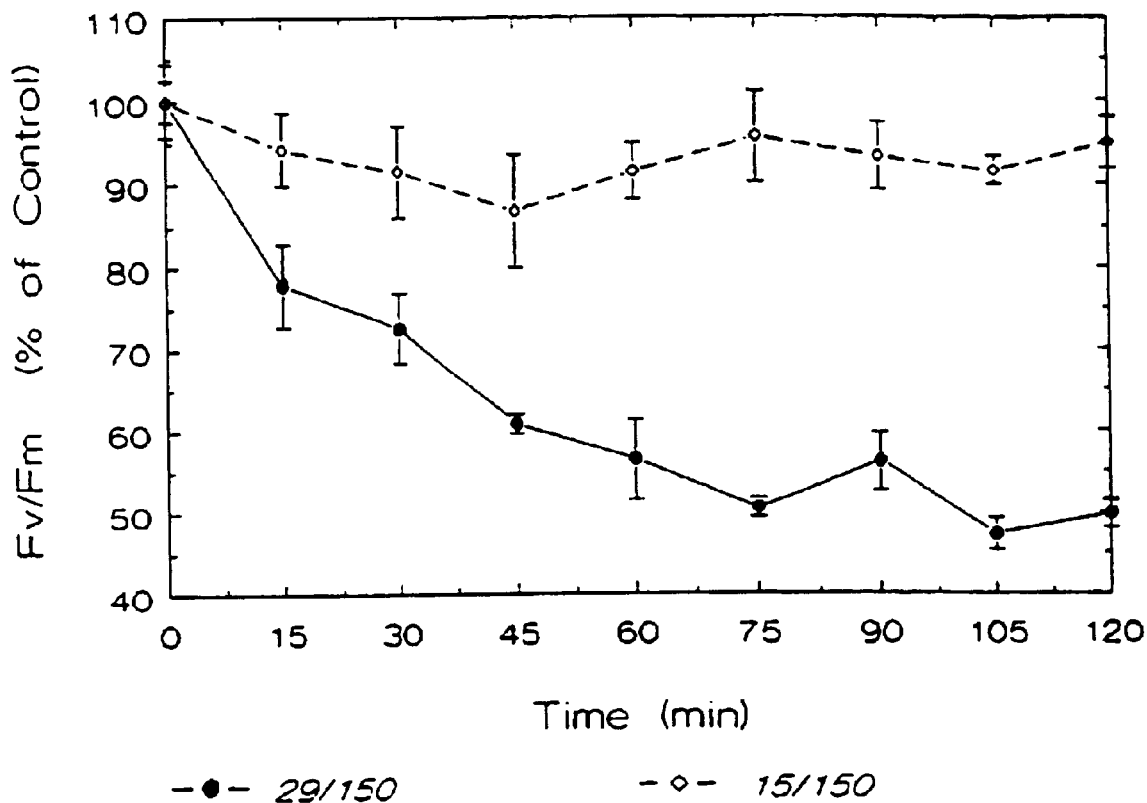
FIG. 2. Effect of UV-A treatment on the efficiency of photosystem II of Plectonema boryanum cultures. Cells were grown either under control conditions (29/150) or exposed to excessive radiation (15/150). Both cultures were then exposed to UV-A radiation and photosystem II efficiency, estimated as the chlorophyll a fluorescence ratio Fv/Fm, was measured as a function of time. All data are presented as a percentage of Fv/Fm of non-treated control cultures. Mean values are calculated from 5 to 7 measurements in 3 to 5 independent experiments.
Figure 3:
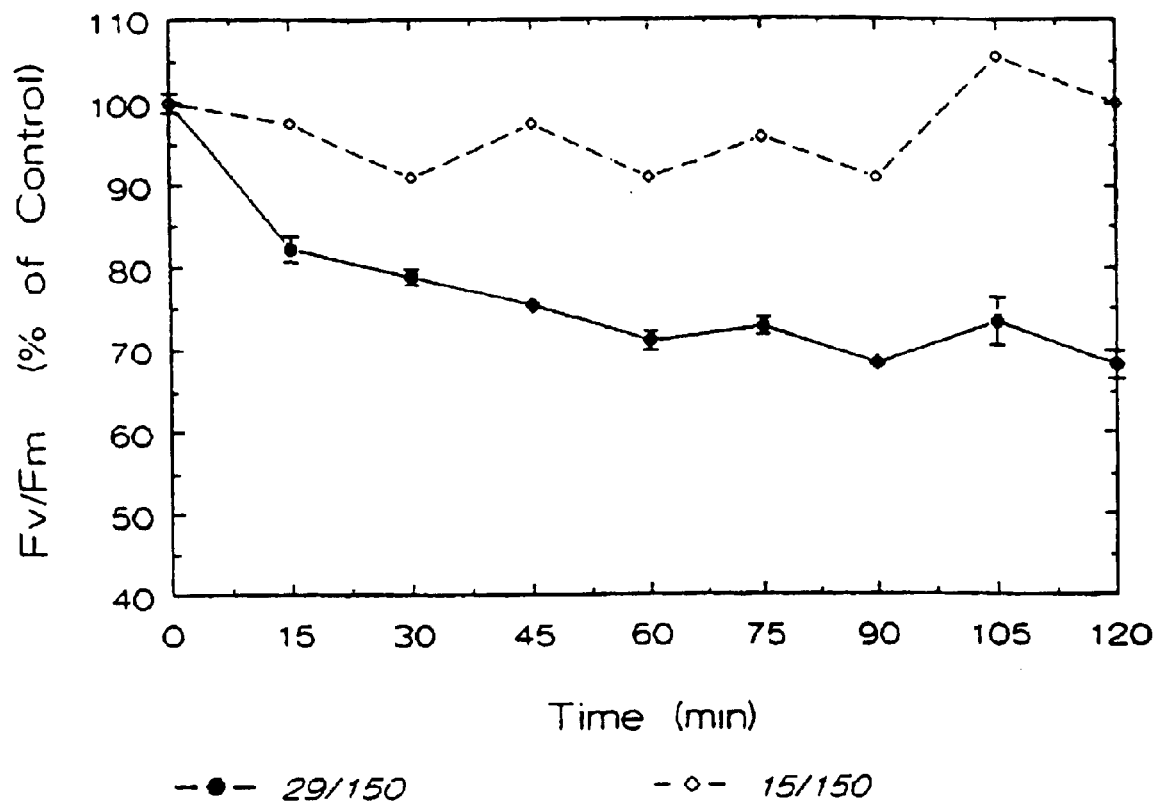
FIG. 3. Effect of UV-A+UV-B treatment on the efficiency of photosystem II of Plectonema boryanum cultures. Cells were grown either under control conditions (29/150) or exposed to excessive radiation (15/150). Both cultures were then exposed to UV-A+UV-B radiation and photosystem II efficiency, estimated as the chlorophyll a fluorescence ratio Fv/Fm, was measured as a function of time. All data are presented as a percentage of Fv/Fm of non-treated control cultures. Mean values are calculated from 5 to 7 measurements in 3 to 5 independent experiments.
Figure 4:
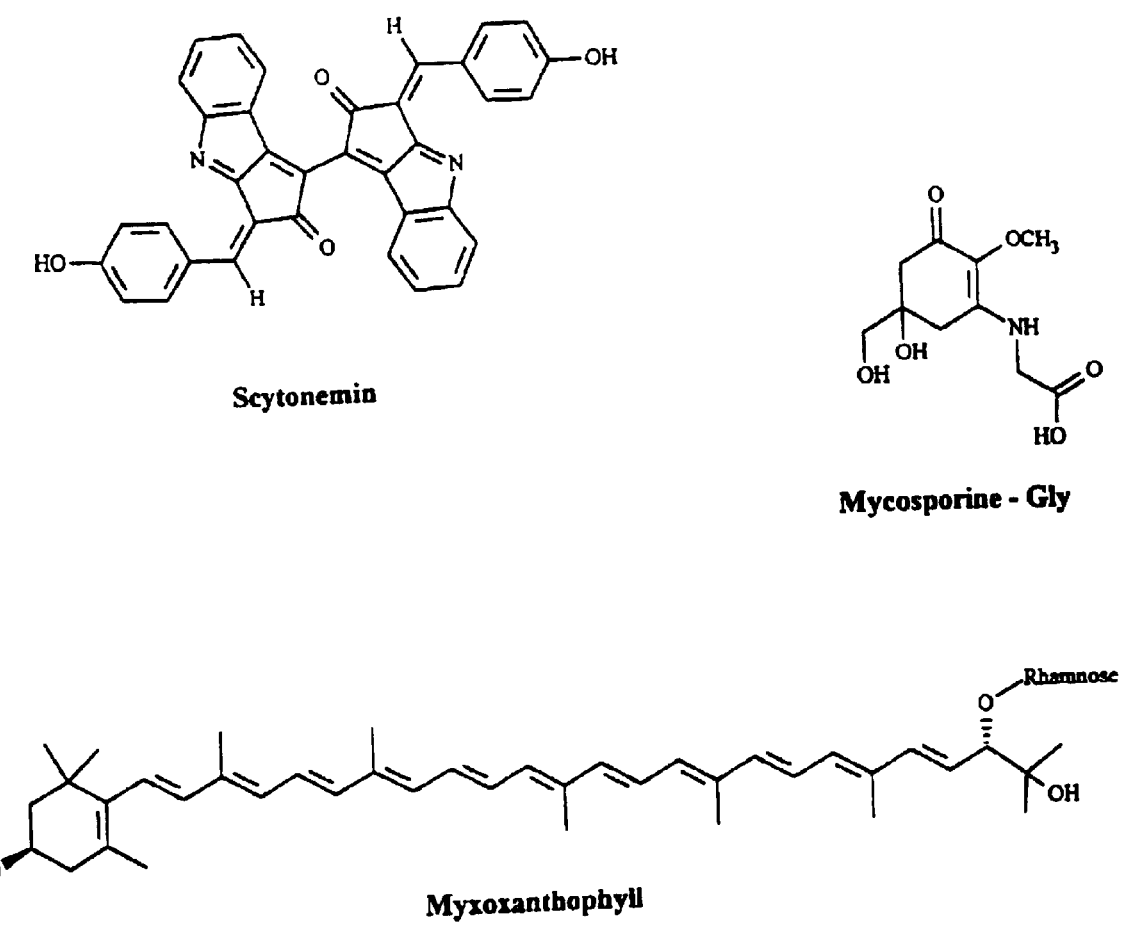
FIG. 4. Chemical structures of scytonemin, mycosporine and myxoxanthophyll.

To show that these cyanobacterial cultures were indeed protected against UV radiation when they had accumulated high levels of myxoxanthophyll, scytonemin and mycosporine, we examined changes in the efficiency of photosystem II when the cyanobacterial cultures were exposed to excessive radiation (FIG. 2). Changes in the efficiency of photosystem II ("PS II") is the most sensitive measure of photodamage to photosynthetic organisms exposed to excessive radiation and can be measured conveniently as changes in the chlorophyll fluorescence ratio, Fv/Fm (Long et al., 1994, Ann. Rev. Plant Physiol. Plant Mol. Biol. 45: 633). Changes in the efficiency of photosystem I ("PSI", for example, as determined by spectroscopy) may also be used as a measure. The results in FIG. 2 illustrate that the efficiency of photosystem II, measured as Fv/Fm, in control, cyanobacterial cells (closed symbols) with low levels of the three protective compounds (29/150), decreased gradually over time of exposure to UV-A. After 90 minutes of exposure to UV-A, the efficiency of photosystem II had decreased to about 50% of initial values and to about 30% after 90 minutes exposure to UV-A+UV-B (FIG. 3, closed symbols). Cells which had been relieved from exposure to excessive radiation (15/6) and hence also accumulated low levels of the three compounds, also exhibited similar sensitivities to UV-A and UV-A+UV-B radiation as controls cultures (data not shown). In contrast, photosystem II efficiency decreased by 5% or less during exposure to either UV-A (FIG. 2, open symbols) or UV-A+UV-B (FIG. 3, open symbols) indicating that the cyanobacterial cultures which accumulated high levels of myxoxanthophyll, scytonemin and mycosporine were virtually completely resistant to UV radiation. Thus, the presence of increased levels of myxoxanthophyll, scytonemin and mycosporine amino acids protects the highly sensitive photosynthetic photosystems of these cyanobacterial cells from excessive UV-A and UV-B radiation. The general chemical structures of these compounds is illustrated in FIG. 4.

These natural compounds and their derivatives make excellent sunscreen agents to protect humans as well as objects from exposure to excessive UV radiation. The mechanism by which we have induced these cyanobacterial cultures to accumulate these compounds appears to be due to the unique interaction of environmental parameters such as light intensity and temperature and not to UV radiation. This is consistent with published data indicating that terrestrial plants as well as algae sense changes in temperature and light through changes in the redox status of PSII, that is, PSII excitation pressure (Maxwell et al., 1995, Plant Physiol. 107:687; Maxwell et al., 1995, Plant Physiol. 109:787; Gray et al., 1997, 114:467; Escoubas et al., 1995, Proc. Nat. Aced. Sci. USA 92: 10237; Dumford and Falkowski, 1997, Photosyn. Res. 53:229). We have also invented a novel method to induce the accumulation of these natural screening compounds in an organism that is very easy to grow and amenable to manipulation by controlling culturing conditions.

In a preferred embodiment, the sunscreen agents that may be used individually, or together, in the compositions include: 1) a cyanobacterial carotenoid, preferrably myxoxanthophyll, 2) a polyphenolic compound, preferrably scytonemin and 3) at least one type of amino acid derivative, preferably a mycosporine amino acid. However, the greatest efficacy for protection against high light and UV radiation occurs when these compounds are present in combination. Each class of compound in this composition absorbs a specific range of light ie. carotenoids in general absorb in the visible range, mycosporine absorbs primarily UV-B and scytonemin absorbs both UV-B and UV-A. These compounds may be isolated from any species of cyanobacteria, such as *Plectonema boryanum*, Gloeocapsa sp., Chlorogloeopsis sp. Scytonema sp. and *Nostoc commune*. The compositions also preferably include a cosmetically acceptable carrier compatible with human skin.

(1) Cyanobacterial Carotenoids

The preferred carotenoids of this invention are the product of cyanobacterial biosynthesis activated under conditions of excessive visible radiation (Ehling-Schulz et Al., 1997, J. Bacteriol. 179:1940). Typical carotenoids include: β-carotene, lutein, neoxanthin, zeaxanthin, violaxanthin, caloxanthin, nostoxanthin, echinenone, canthexanthin, antheraxanthin, and oscillaxanthin. The preferred compounds are, among others, echinenone and myxoxanthophyll (FIG. 4). In this application, the term carotenoid includes both single species of carotenoid and a mixture of several carotenoids.

(2) Polyphenolic Compounds

Scytonemin or one of its conjugates is the preferred polyphenolic compound (FIG. 4). It is a yellow, lipid-soluble pigment with an in vivo absorption maximum of 370 nm and has a structure based on indolic and phenolic subunits (Proteau et al., 1993, Experentia 49:825; Ehling-Schulz et al., 1997, 179: 1940; Garcia-Pichel et al., 1992, Photochem. Photobiol. 56: 17). In this application, the term polyphenolic compound includes both a single species of polyphenolic compound and a mixture of several polyphenolic compounds.

(3) Mycosporine Amino Acids

Mycosporine is a general term for a group of about 10 to 12 compounds that exhibit the general structure shown in FIG. 4. All mycosporines have the central ring structure shown with various amino groups modifying this ring structure. Mycosporine amino acids represent a relatively broad class of water-soluble substituted cyclohexenes that are linked to amino acids and iminoalcohols and have absorption maxima between 310 and 360 nm. The term mycosporine in this application includes both a single species of mycosporine compound and a mixture of several mycosporines (Garcia-Pichel et al., 1992, J. Bacteriol. 56: 17; Garcia-Pichel et al., 1993, Applied Environ. Microbiol. 59: 170; Ehling-Schilz et al.,1997, J. Bacteriol. 179: 1940; Xiong et al., 1997, Physiol. Plant. 100: 378; Karsten et al., 1998, Phycological Res. 46: 271). All of the compounds commonly referred to as mycosporine are included within the scope of the invention. Typical mycosporine amino acids include: mycosporine-glycine, palythine, asterina-330, palythinol, palythene, porphyra-334, mycosporine-glycine:valine, shinorine and MAA 357.

(4) Alternative Compositions

Alternative compositions of the invention include sunscreen agents from other organisms, such as plant, algal, fungal and bacterial sunscreen agents.

Carotenoids, polyphenolic compounds and mycosporine amino acids from plants, green algae and cyanobacteria may also be used together or individually in the compositions. Carotenoids, as a general class of pigments, are found in all photosynthetic organisms including plants, green algae, cyanobacteria and photosynthetic bacteria. Although the polyphenolic scytonemin is particular to cyanobacteria, plants as well as green algae produce other polyphenolic compounds that act as potential UV screening compounds. Mycosporine amino acids are found in a myriad of Antarctic marine organisms and are of similar structure independent of its biological source (Karentz et al., 1991, Mar. Biol. 108: 157). Amino acids that absorb solar radiation adequately, such as tyrosine and tryptophan, are also useful in the compositions of the invention.

Certain species of heterotrophic organisms (such as certain fungi and bacteria) produce carotenoids to protect themselves from light. However, these organisms do not produce these pigments in response to excitation pressure.

They may produce these compounds in response to UV exposure or other photobiological signals. The invention also includes carotenoids or pigments from either photosynthetic or heterotrophic (ie. non-photosynthetic) organisms, for example *Deinococcus radiodurans*, which produces a carotenoid which is a xanthin, called deinoxanthin. It is also possible to use extracts of these organisms in sunscreen compositions.

Modification of Cyanobacterial Sunscreen Agents and Related Sunscreen Agents

Compounds similar to the carotenoid, polyphenolic compounds, mycosporine amino acids (and light absorbing amino acids such as tryptophan and tyrosine) and other sunscreen agents of the invention described in this application may also be used in the compositions. Derivatives may be prepared by the following general methods and procedures as well as other procedures known in the art. For example, carbonyl groups on scytonemin and mycosporine may be reduced or reductively aminated to give an alcohol or an amine compound. Optionally, these alcohol or amine compounds can be further derivatized by reaction with, for example, acyl halides, acyl anhydrides, halo formates and isocyanates to afford esters, amides, carbonates, ureas and the like. Amine compounds can also be reductively alkylated with aldehydes and ketones to from secondary amines. Such derivatization reactions of alcohols and amines are well known and can be accomplished using known procedures (Organic Chemistry, 1967, Morrison and Boyd, Second Edition). The alcohol groups on mycosporine, scytonemin and myxoxanthophyll may be modified using similar techniques. The water or lipid solubility of the compounds may be changed by either removing or conjugating the compounds with sugars, oligosaccharides, fatty acids, fatty alcohols, amino acids, peptides and protein modifications. These derivatives can be assayed using known techniques and techniques described in this application to determine their ability to absorb light and their usefulness in the compositions of the invention. When the compounds are intended for use on mammalian skin (e.g. humans) they may be tested for compatibility with skin using known methods.

Extracts

The present invention shows that extracts of photoautotrophs, such as photoautotrophic bacteria (eg. cyanobacteria) can be incorporated into sunscreen compositions. Heteroautotrophic bacteria may also be used. The extracts may be aqueous extracts or hydroalcoholic extracts. The extracts are preferably present in amount necessary to give the desired protection from solar radiation. These amounts would be apparent to one skilled in the art. For example, the amounts of extracts in the formulated sunscreen composition may range from 0.001 to 25% by weight, 0.1% to 25% by weight, 0.1% to 10%, 0.1% to 5%, 0.1% to 1% or 0.5% to 5%. For example, the cyanobacterial extracts can be made by treating the photoautotrophic cells, such as cyanobacteria, with extraction agents by methods known in the art Useful extraction agents may include water, mineral oil, hydrocarbons, silicones, fatty acids, fatty acid derivatives, waxes, oils, ketenes and mixtures thereof. For example, water and an aliphatic alcohol, such as ethanol may be used. Hydrophobic extraction agents, as well as hydrophilic extraction agents may be employed. Such agents can include fatty acids, esters, diesters, triesters, hydrocarbons, waxes or silicones. Hydrophilic agents can include water and low molecular weight aliphatic alcohols. Other extraction agents will be apparent to those skilled in the art.

Preferably, in the present invention, the cyanobacterial extract is derived by extraction in methanol and acetone. Useful extracts may also be obtained from photosynthetic bacteria, plants and algae. The foregoing procedure may be adapted as necessary and applied to these organisms. The invention includes methods of preparing sunscreen compositions by producing extracts from photoautotrophs, photoautotrophic bacteria (such as cyanobacteria), heteroautotrophic bacteria and other organisms and formulating the extracts in a sunscreen composition (the active ingredients may be separated from the extracts). The invention also includes a method of identifying a composition or an agent with sunscreen activity by preparing an agent or a composition, such as an extract, from one of the aforementioned organisms and determining the ability of the agent or composition to act as a sunscreen by measuring its sunscreen activity. Techniques described in this application may be used to identify sunscreen activity.

Formulation of Sunscreen Compositions

A large number of efficient formulation methods for sun care products have been reported during the past twenty years (Flick, 1984, Cosmetic and Toiletry Formulations, pp 513, Noyes Pub., New Jersey; Gasparro et al., 1998, Photochem. Photobiol. 68:243). Sunscreen products may include a wide range of ingredients that do not absorb solar radiation but help to control characteristics such as film thickness, opacity, rub resistance, water proofing and uniformity. The sunscreens agents of the invention, carotenoids, such as myxoxanthophyll, and/or polyphenolic compounds, such as scytonemin and/or mycosporine amino acids or derivatives of these compounds are formulated with known compounds in order to obtain sunscreens with desired properties (Sun Care Products Formulary, 1998, Cosmetics and Toiletries 113:83).

The preferred concentrations for myxoxanthophyll are 0.02 to 20 mg by weight and more preferably 0.5 to 5 mg by weight. The preferred concentrations for scytonemin are 0.01 to 10 mg by weight and more preferably 0.1 to 2 mg by weight. The preferred concentrations for mycosporine amino acids or other light absorbing amino acids are in the range 0.01 to 10 mg by weight and more preferably 0.1 to 2 mg by weight. Suitable masses and concentrations for other sunscreen agents disclosed may be determined by those skilled in the art using known techniques The compounds of the invention are also useful for integration into other articles exposed to sunlight to prevent photodestruction and photobleaching. The following specific examples are presented to illustrate more particularly the invention and are not to be construed as limitations.

(1) Formulation of a UV-Blocking Cream or Other Composition

The formulated sunscreens preferably containing myxoxanthophyll, scytonemin and mycosporine amino acids are preferably prepared in a phosphate based emulsifying system combined with long chain esters such as lignoceryl erucate to confer water resistance and controlled spreading when applied to the skin. Compositions are also formulated according to other techniques well known in the art, in particular techniques for preparation of oil-in-water or water-in-oil emulsions. The specific amount of sunscreen compounds needed to obtain a desired sun protection factor (SPF) can be determined by those skilled in the art. The SPF may be determined according to known techniques. The preferred SPF is at least 2.

Other useful carriers include any of gases, water, water-based liquids, lotions, dispersions, oils, oil-based solutions, powder, gels, emulsions, dispersions or mixtures thereof. The appropriate amount of carrier can readily be determined by those skilled in the art according to the SPF desired. Hydrophobic carriers as well as hydrophilic carriers may be employed with the sunscreen compositions. Carriers to be applied to the skin or hair are compatible with human skin or hair, respectively.

Additional sunscreen agents known in the art may also be added to the compositions, for example at least one additional hydrophilic or lipophilic organic UV-A and/or UV-B sunscreen agent. The compositions of the invention may also include, in addition, conventional cosmetic adjuvants and additives such as preservatives, organic solvents, browning agents, antioxidants, stabilizers, emollients, silicones, alpha-hydroxy acids, demulcents, anti-foaming agents, moisturizing agents, vitamins, fragrances, ionic or nonionic thickeners, surfactants, fillers, thickeners, sequestrants, polymers, propellants, alkalinizing or acidifying agents, opacifiers, fatty compounds (eg. oil, wax, alcohols, esters, fatty acids), colorants, or mixtures thereof or any other ingredient that may be used in cosmetics and in particular for the production of sunscreen compositions.

The invention also relates to a method of protecting human skin or hair against the deleterious effects of solar radiation by topically applying thereto an effective amount of a composition of the invention.

(2) Formulation of the 'Cyanos-cream'

Plectonema boryanum was cultured under conditions of high excitation pressure ie. low temperature (15° C.) and moderate irradiance (150 $\mu$mol m$^{-2}$ s$^{-1}$) to maximize the production of myxoxanthophyll, scytonemin and mycosporine. Subsequently, the cells were concentrated by centrifugation and extracted.

The steps to obtain the crude pigment extract consist of: break cells using dry ice or liquid nitrogen; extract the lysate using 100% methanol; isolate the pigments from the methanol solution; evaporate the methanol. The remaining material is called crude pigment extract. One may also formulate purified compounds. Compounds are separated and purified using techniques known in the art, such as high pressure liquid chromatography (HPLC).

A suitable formulation base is Glaxal base (Roberts; Dermatological Base-Emollient). Glaxal base is a water miscible, nongreasy, nonmedicated, hypoallergenic, lanolin free base used for the preparation or dilution of dermatological creams and ointments. The active ingredients include: 4-chloro-m-cresol 0.1%, cetomacrogol 1 000 1.8%, cetostearyl alcohol 7.2%, paraffin 15%, petrolatum liquid 6%. Any emulsion, cream, lotion, spray that is either an oil/water or a water/oil base is a suitable base may be used. Prefered bases are compatible with human skin and/or hair. Other suitable bases will be apparent. 0.5% weight/weight of the crude pigment extract were added to the base to form the "sunscreen lotion". The preferred masses described elsewhere in this application may also be used.

(3) Formulation of a Personal-care Product with UV-screening Compounds.

Compositions for hair or other personal care may be prepared by adding UV screening compounds in hair rinses, aerosol sprays, mists, gels, mousses, shampoos, conditioners, lotions, films, emulsions and colouring products to reduce photodamage to hair and photobleaching of hair and hair dyes. The invention also relates to a method of protecting human hair against the deleterious effects of solar radiation by topically applying thereto an effective amount of a composition of the invention.

Makeup products such as foundation, lipstick, eyeshadow, blush, nail polish, mascara, moisturizing creams and lotions or eyeliner may also contain the compounds of the invention. These are formulated according to known methods for makeup products such as those for preparation of an anhydrous or aqueous solid or paste, emulsion, suspension or dispersion.

(4) Formulation of Car Windshields, Solar Panels, Solarium and Building Windows with UV-screening Compounds.

Car windshields, solar panels, solarium and building windows and other glass, plexi-glass, transparent polymer, plastic or similar products may be impregnated with UV-screening compounds or covered by a membrane impregnated with UV-screening compounds to protect biological organisms, plants and objects from exposure to UV radiation.

(5) Formulation of Eyewear Products with UV-screening Compounds.

Eye glasses, contact lenses and lens implants may be impregnated with UV screening compounds or covered with a membrane impregnated with UV screening compounds to protect eyes from exposure to UV-radiation.

(6) Formulation of Transparent Shields with UV-screening Compounds for use in Space Travel Transparent shields and windows for use in space vehicles and space stations may be impregnated with UV-screening compounds to protect biological organisms, plants and objects from exposure to UV-radiation.

(7) Formulation of Protective Coatings with UV-screening Compounds.

The sun screen compounds may be incorporated into a variety of paints, stains, coloring compositions, lacquers and similar coatings to prevent premature photodamage and photobleaching to surfaces of objects.

(8) Formulation of Foliar Sprays with UV-screening Compounds.

The sun screen compounds may be mixed with foliar sprays containing either herbicides, pesticides or plant growth substances such as hormones, auxins, gibberellins, abscisic acid, cytokinins and/or their derivatives to prevent photodegradation of the herbicides, pesticides or plant growth substances such as auxins, gibberellins, abscisic acid and/or their derivatives. Similar compositions may be prepared for animals, such as mammals.

Overproduction of Screening Compounds

The invention also relates to methods for inducing cyanobacterial cultures to over-produce the screening compounds of the invention by growing the cultures under high excitation pressure. This refers to the manipulation of photosystem II efficiency by altering its inherent oxidation-reduction state. We have shown that myxoxanthophyll is the primary carotenoid accumulated in Plectonema boryanum which is localized almost exclusively in the cell wall of this filamentous cyanobacterium. We have shown for the first time that the accumulation of myxoxanthophyll, scytonemin and mycosporine amino acids are a response to growth at high excitation pressure rather than UV-radiation. This high excitation pressure can be created for example either by keeping the growth irradiance constant and lowering the growth temperature or by keeping the growth temperature constant and increasing the growth irradiance in the absence of UV-radiation. The accumulation of these compounds makes the cultures totally resistant to UV-A and UV-B radiation based on the measurement of photosystem II efficiency (FIGS. 2 and 3). Where typical or preferred process conditions (e.g., reaction temperatures, times, mole ratios of reactants, solvents, pressures, etc.) are given in this application, other process conditions may also be used.

Optimum conditions may vary with the particular cultures, nutrients or reactants used, but such conditions can be determined by one skilled in the art by routine optimization procedures. Sunscreen compound production may be induced in plants (preferably higher plants), algae and other organisms containing chlorophyll a or b, using similar methods and known methods in the art.

Cyanobacteria, such as *Plectonema boryanum*, may be induced to accumulate high levels of myxoxanthophyll, scytonemin and mycosporine by simply growing the cultures at either moderate irradiance (150 $\mu$mol m$^{-2}$ s$^{-1}$) and a temperature of 15° C. or at a moderate temperature of 29° C. and high light (750 $\mu$mol m$^{-2}$s$^{-1}$). Thus, we exploit these rapidly growing cyanobacteria as a natural source of these screening compounds. We culture the cyanobacteria under conditions which maximize production of myxoxanthophyll, scytonemin and mycosporine in the shortest possible time.

One important factor that constrains the efficiency and capacity to produce these compounds biologically is growth temperature. The lower the growth temperature, the slower is the rate of growth of the cells and, therefore, the slower the rate of production of the compounds of interest. In fact, growth temperature and not growth irradiance is the major factor limiting growth rates of *Plectonema boryanum* (Miskiewicz and Huner, unpublished). However, low growth temperature is required for maximum production of the screening compounds. Since the growth rate of *Plectonema boryanum*, measured as dry matter production, has a $Q_{10}$ of about 2 between 15° C. and 30° C., an increase of only 1° C. in growth temperature has a potential to increase cell dry matter production by about 10%. We may determine the optimum growth temperature for the maximum production of myxoxanthophyll, scytonemin and mycosporine with the batch culture method presently used in the laboratory. Growth irradiance (150 $\mu$mol photons m$^{-2}$ s$^{-1}$) and inoculum concentrations remain constant and growth temperature varied between a high temperature of 29° C. and a low temperature of 15° C. Pigments are preferably extracted in acetone, separated, quantified on a per gram cell dry weight basis by HPLC as described in detail previously (Maxwell et al., 1995, Plant Physiology 107:687). Scytonemin and mycosporine amino acids are extracted in methanol and then quantified spectrophotometrically. Subsequently, mg screening compound produced per gram cell dry weight is plotted against growth temperature to determine optimum growth temperature for maximum production of the screening compounds.

The accumulation of the screening compounds in *Plectonema boryanum* is a response to increased PSII excitation pressure. Thus, we increase further the production of these screening compounds at the optimum temperature by increasing the growth irradiance. After the optimum growth temperature for production is established, the optimum irradiance for production is assessed. The growth temperature is held constant at the optimum determined above and growth irradiance varied between 150 and 750 $\mu$mol photons m$^{-2}$ s$^{-1}$. Subsequently, mg quantities of screening compound produced per gram cell dry weight is plotted against growth irradiance to show optimum growth irradiance for the maximum production of the screening compounds. Thus, the optimum growth temperature and growth irradiance conditions allow us to maximize production of the compounds of interest. From the known growth time, the rate of production is calculated as mg screening compound per gm cell dry weight per hour. From the known photon flux used for the production of the screening compounds, we calculate the efficiency of production as mg screening compound accumulated per gm cell dry weight per hour per photon absorbed.

We also scale up culture production to maximize the volume of the culture vessels and to maximize dry weight production. Larger culture vessels maintain a homogeneous distribution of light of sufficient intensity to create sufficient excitation pressure to induce the cells to produce the screening compounds. Second, the vessel includes a water jacket to maintain constant low temperature (15° C. in the case of *P. boryanum*).

Scytonemin and mycosporine are not specific to the filamentous cyanobacterium, *Plectonema boryanum*. Other species of cyanobacteria known to produce scytonemin and mycosporine are useful sources of the screening compounds when exposed to high PSII excitation pressure. Employing the same or similar growth conditions for the production of the screening compounds In *P. boryanum*, we produce sunscreening compounds in the following filamentous cyanobacteria Gloeocapsa sp.(Garcia-Pichel et al., 1993, Applied Environ. Microbiol. 59:170), Chlorogloeopsis sp. (Garcia-Pichel et al., 1992, Photochem. Photobiol. 56:17), Scytonema sp (Proteau et al., Experentia 49:825) and *Nostoc commune* (Ehling-Schulz et al., 1997, J. Bacteriol. 179:1940). Since the latter flourishes under extremely cold conditions, this species is ideal for the production of the screening compounds under high PSII excitation pressure. In addition, we produce sunscreen compounds in the unicellular cyanobacterial species *Synechocystis* and *Synechococcus* sp. Concomitantly, we also assess the resistance of these species to UV-radiation relative to *P. boryanum* as described above (FIGS. 2 and 3).

These procedures are adapted for overproduction of screening compounds in other organisms that produce sunscreen agents described in this application.

Biological Assay for Sunscreen Protection

Sun protection factor (SPF) is used generally as a measure of protection against skin bum due to UV-B radiation. SPF is defined as the ratio of skin bum due to sun exposure that skin can tolerate with and without sunscreen protection. Thus, SPF is a measure of protection against sunburn due to UV-B exposure but does not reflect the damaging effects of exposure to UV-A. As a consequence, the inherent value of this measure to estimate sunscreen efficacy has come into question recently (Gasparro et al., 1998, Photochem. Photobiol. 68: 243). We use a sensitive, relevant, biological assay to assess the efficacy of various compounds to protect against UV-radiation. This is accomplished by exploiting the sensitivity of either cyanobacterial, algal or plant photosystem II to UV-radiation. The sensitivity of cyanobacterial photosystem II to UV-radiation (see FIGS. 2 and 3) is useful in an assay to assess the protective qualities of a potential sunscreen agent or a formulated UV-screening cream. The agents are preferably tested using an artificial filter of cyanobacterial extract (or an extract from a plant, algae or photosynthetic bacteria). Protection from UV damage provided by the artificial filter is assessed by monitoring changes in the photosystem II efficiency of the cyanobacterial culture using the chlorophyll fluorescence parameter, Fv/Fm. This test is useful to cosmetic or pharmaceutical companies to test the efficiency of UV screening agents.

The advantages of the cyanobacterial or algal culture assays include speed, simplicity, reproducibility and low cost. The cyanobacterial or algal culture assays will replace or supplement more expensive and complex animal models currently in use in the cosmetic and pharmaceutical industries. Although cyanobacterial cultures are likely to be the easiest organism to use to assay the effects of UV-screening compounds by monitoring the efficiency of photosystem using chlorophyll fluorescence ratio (Fv/Fm) these assays are conducted using algae, lichens, higher plants and any other organism containing chlorophyll a.

Assessment of the Extracted Screening Compounds to Protect Against UV-A and UV-B Radiation To show efficacy of extracts containing myxoxanthophyll, scytonemin and mycosporine and the other compounds of the invention to protect against UV-radiation, we create an artificial filter using a cyanobacterial extract. For example, cyanobacteria grown under conditions where the screening compounds do not accumulate (either 29/150 or 15/6) are exposed to UV-A+UV-B radiation as performed in experiments illustrated in FIGS. 2 and 3 above. Between this culture and the UV source, an artificial filter consisting of the base only is placed. Concomitantly, an artificial filter containing the extracted screening compounds at a known concentration is placed between an identical culture and the UV source. The effects of exposure to the UV radiation at 29° C. is assessed by monitoring changes in photosystem II efficiency through changes in the ratio of Fv/Fm as a function of exposure time as illustrated in FIGS. 2 and 3. Thus, the cells under the artificial filter containing the screening compounds are protected from the UV-radiation compared with identical cells associated with the artificial filter containing only the base. UV damage is quantified by the decrease in Fv/Fm and/or by changes in other chlorophyll fluorescence parameters such as Fo, Fo', Fm', Fv', Fv'/Fm', qp and qn, during or following exposure to UV-radiation. We used a similar approach successfully to test the capacity of plant anthocyanin, a red flavonoid accumulated specifically in leaf upper epidermal cells, to protect leaves from excess irradiance (Krol et al., 1995, Can. J. Bot. 73: 1119). The optimum concentration and ratios of myxoxanthophyll: scytonemin: mycosporine required for maximum protection against UV-radiation are determined. Similar assessments are completed for other sunscreen compounds described in this application.

We also determine the stability of the extracted compounds to visible light as well as UV-radiation as a function of time. In our work with plant anthocyanins (Krol et al., 1995, 73: 1119 ), we stabilized the extract by altering the solvent and pH. The breakdown of myxoxanthophyll, scytonemin and mycosporine is monitored first by changes in their visible and UV absorption spectra as well as by a decrease in the ability of the liquid filter containing these compounds to protect cells against the UV-radiation as indicated by increased photoinhibition of cyanobacterial cultures that do not contain these screening compounds. We now stabilize the extracted screening compounds initially by altering solvent, solvent concentrations and pH.

Bioassay to Assess UV Protection

Figure 5:
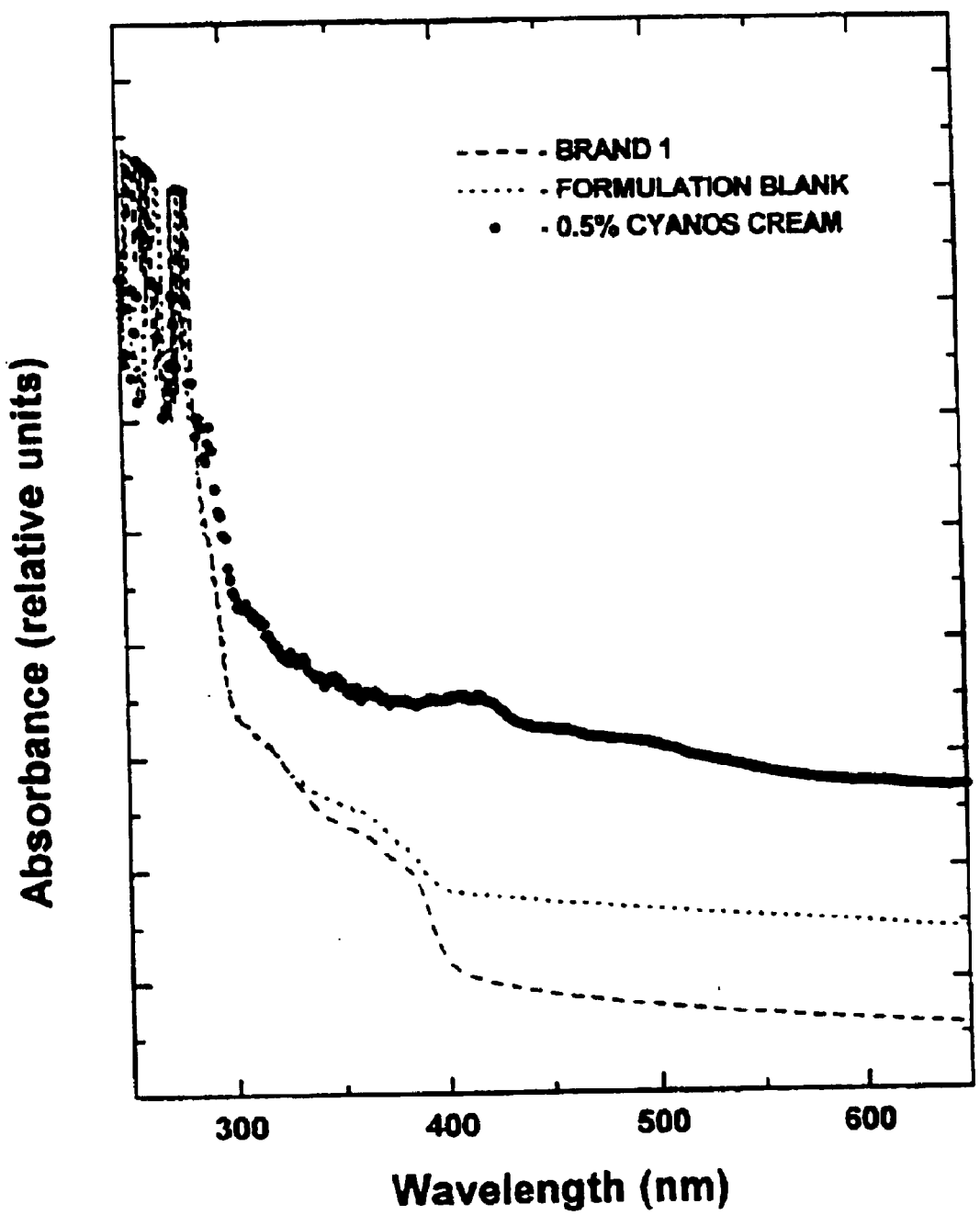
FIG. 5. Absorption spectra of commercial UV sunscreen creams (BRAND 1 and BRAND 2) and 0.5% CYANOS CREAM.

Control cultures of *Plectonema boryanum* were grown at high temperature (29° C.) and moderate irradiance (150 $\mu$mol m$^{-2}$ s$^{-1}$) to ensure minimal production of myxoxanthophyll, scytonemin and mycosporine and thus maximal sensitivity to UV radiation. Control cultures were transferred axenically to disposable Corning polystyrene culture flasks with a stirring bar to keep the cells suspended. The surface of the culture flask was covered in black tape except for a small area A known amount (0.3 gm) of either a commercially available sunscreen, the 0.5% 'cyanos-cream' or the FORMULATION blank consisting of the carrier only was applied and spread evenly over this area of the culture flask. The UV-visible absorption spectra of a commercially available sunscreen (Brand 1), the 0.5% 'cyanos-cream' and the formulation blank (the carrier used for the 'cyanos-cream') on the surface of the culture flask are illustrated in FIG. 5. Even though Brand 1 had a reported SPF of 15, its absorption of UVB and UVA radiation between 280 and 400 nm is comparable to that of the carrier employed in the 'cyanos-cream'. The active UV absorbing agent in Brand 1 was present at a concentration of 8%. In contrast to Brand 1, the 0.5% 'cyanos-cream exhibited significantly greater absorption not only in the UVB-UVA region of the spectrum (280 to 400nm) but also in the visible region of the spectrum (400 to 650 nm). Thus, the 0.5% 'cyanos-cream' exhibited greater UV absorption than the commercially available cream (Brand 1) even though the active absorbing agents in the 'cyanos-cream' were present at a 16-fold lower concentration than the active ingredient in Brand 1.

Purification of Screening Compounds

UV screening compounds are preferably used as crude extracts or partially purified extracts obtained from chlorophyll containing organisms. These screening compounds may also be purified. Extracts and sunscreen compounds are preferably further purified preferably by preparative HPLC. For example, semi-purified extracts are dissolved in chloroform/methanol and injected onto preparative HPLC columns (30=100 cm) containing high-resolution silica gel ( 200–400 mesh) particles. Solvent is pumped through the column using a Kiloprep Waters preparative HPLC system. Fractions containing myxoxanthophyll, scytonemin and microsporine are detected using a UV/visible flow detector, collected and the solvent evaporated in vacuo.

Purified material is tested on cyanobacterial cultures as a UV screen using the liquid filter method as described above. Because myxoxanthophyll is by far the most abundant material produced by the cyanobacteria, it is extensively purified and used as a UV screen. Fractions containing mixtures of scytonemin and mycosporine are also used to screen out UV radiation separately as well as in combination with myxoxanthophyll. Similar procedures are used to purify the other sunscreen compounds described in this application.

Further experiments (1) show the validity of the biological assay to assess protection against UV-induced damage and (2) test the ability of a formulation ('cyano-cream'), derived from a crude extract of *Plectonema boryanum* cultured under high excitation pressure (15° C./1590 $\mu$mol m$^{-2}$ s$^{-1}$), to protect control cultures of cyanobacteria against UV-induced damage relative to commercially available sunscreens of known SPF.

These culture flasks with the control suspensions of *Plectonema boryanum* and containing either no cream (control sample) or 0.3 gm of 'cyanos-cream' spread over a surface area of 9.45 cm$^2$ were subsequently exposed to UV radiation at 25° C. for up to 2 hours. Samples of the cell suspension were removed every 30 minutes to assess PSII photochemical efficiency measured as Fv/Fm (FIG. 26A). In the absence of any cream on the surface of the culture flask (FIG. 26A, closed squares), the Fv/Fm ratio decreased by about 50% after 2h exposure to UV radiation indicating damage to the photosynthetic apparatus. In contrast, in the presence of the 0.5% 'cyanos-cream' on the surface of the culture flask (FIG. 28A, closed circles), the Fv/Fm ratio of the Plectonema suspension decreased by only 10% after 2 h exposure to UV radiation indicating a significant protection against UV radiation-induced damage. When 0.3 gm of the carrier (formulation blank) was spread on the surface of the culture flask, no protection against UV radiation was observed. This shows that the protection against the UV radiation imparted by the 0.5% 'cyanos-cream' is due to the cyano-extract incorporated into the formulation.

Figure 6:
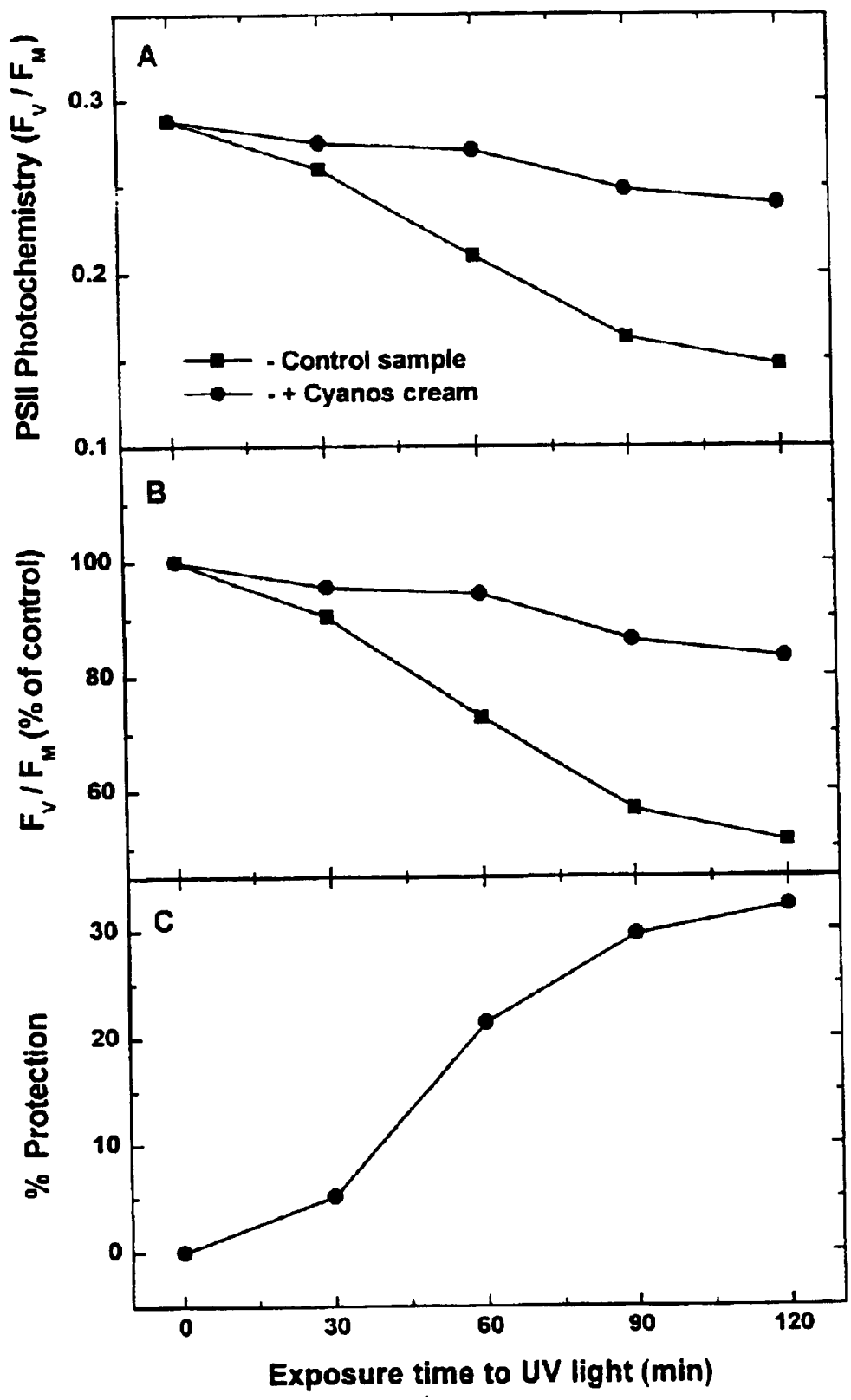
FIG. 6. A. Effect of CYANOS CREAM (0.5%) on the UV light—induced deterioration of PSII photochemistry measured as Fv/Fm in P. boryanum cell culture. B. Exposure time effects of UV light on the Fv/Fm in control sample and sample protected by CYANOS CREAM. The data are presented as a percentage of non-UV treated samples. C. Protection effect of CYANOS CREAM calculated as a difference between the Fv/Fm values of cells protected by CYANOS CREAM (+CYANOS CREAM) and control sample.
Figure 7:
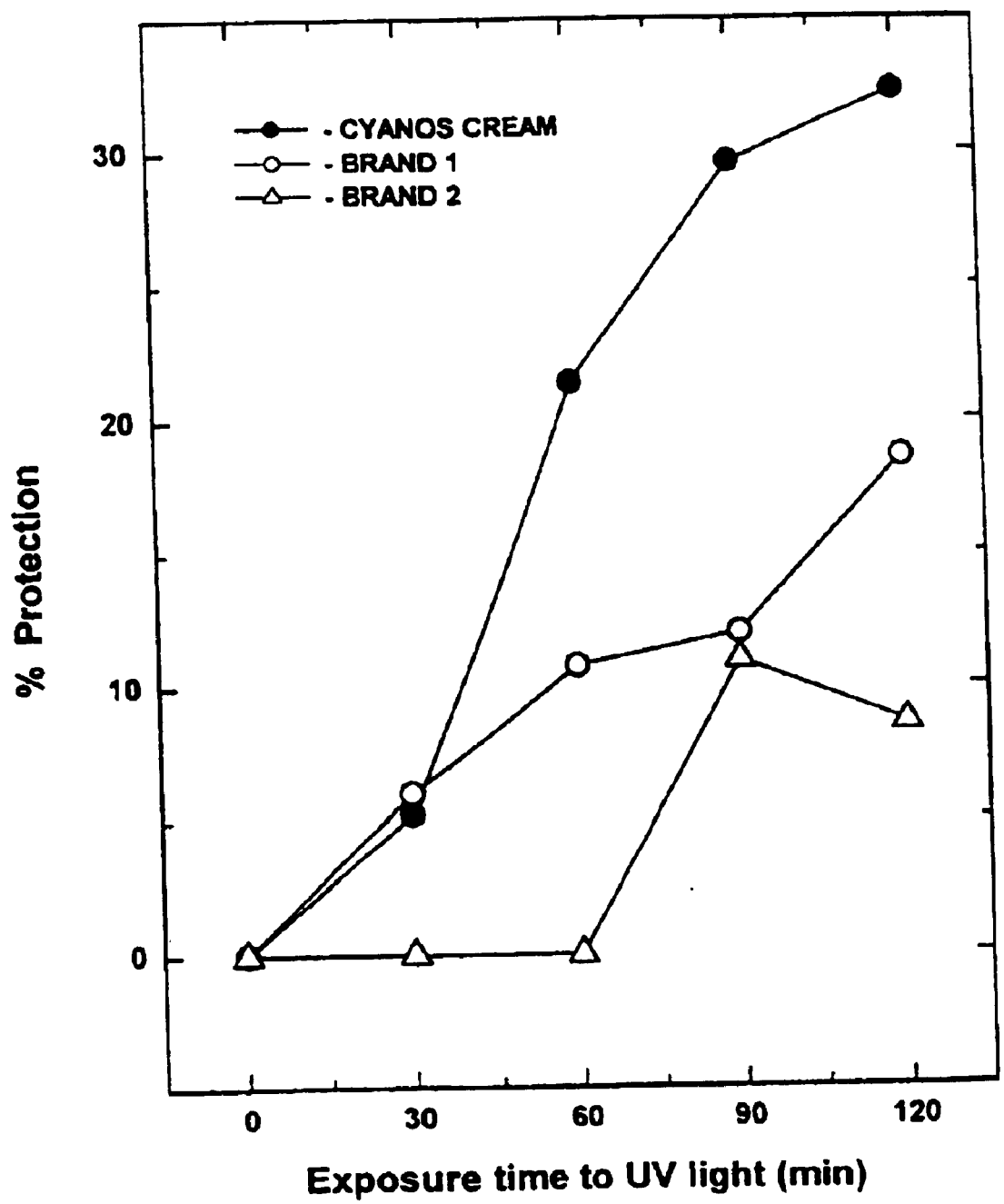
FIG. 7. Exposure time dependent protection against UV light of commercial UV sunscreen creams BRAND1 and BRAND 2 and the CYANOS CREAM. All creams were applied by spreading 0.3 gm of cream over a fixed area ( 9.45 cm$^2$) of the polystyrene culture flask. This resulted in a standardized application of 0.032 gm of cream / cm$^2$. The amount of cream used and the surface area may be varied.

FIG. 6B illustrates the same data as illustrated in FIG. 6A but normalized to the initial Fv/Fm value of the Plectonema suspension prior to exposure to the UV radiation. From the normalized data we calculated the % protection imparted by the 0.5% 'cyanos-cream' relative to the control, unprotected sample during the 2 h exposure to the UV radiation (FIG. 6C). The % protection was calculated by subtracting the Fv/Fm value of the control samples (FIG. 6B, closed squares) from the Fv/Fm value of the sample with the 0.5% 'cyanos-cream' (FIG. 6B, closed circles) at each time of exposure to the UV radiation. Thus, after 2h exposure to UV radiation, the 0.3 gm of the 0.5% 'cyanos-cream' provided 30% greater protection than either no cream or 0.3 gm of the carrier. We conclude that the 0.5% 'cyanos-cream' does indeed protect the cyanobacterial culture against damage due to UV radiation. Furthermore, we conclude that our bioassay which assesses the UV-induced damage to the photosynthetic apparatus via the standard chlorophyll fluorescence ratio, Fv/Fm, is a sensitive and useful assay for UV damage. An added advantage of this bioassay is that it is relatively inexpensive, easy to perform and circumvents the use of animals to assess UV damage. The assay may be used to test other compositions in addition to sunscreen, such as makeup and the other compositions listed in this application.

The protection against UV-induced damage provided by the 0.5% 'cyanos-cream' is superior to that provided by commercially available sunscreens of known SPF. To show this, we purchased two sunscreen creams available from two different manufacturers. Both Brand 1 and Brand 2 were labelled as exhibiting an SPF of 15. In both cases, the active UV absorbing Ingredient was present at a concentration of 8%. Using the same bioassay as described above, we compared the capacity of 0.3 gm of either Brand 1, Brand 2 or the 0.5% 'cyanos-cream' to protect a suspension of *Plectonema boryanum* against UV damage. The results illustrated in FIG. 37 indicate that the 0.5% 'cyanos-cream' imparted 2 to 3 times greater protection after 2 h of exposure to V radiation than either Brand 1 or Brand 2 respectively. This higher level of protection was provided by the 'cyanos-cream' despite the fact that the concentration of the active ingredients in the 'cyanos-cream' (0.5%) is 16-fold lower than that present in either Brand 1 or Brand 2 (8%). These data are consistent with the absorption spectra presented in FIG. 1. Furthermore, we conclude that the 0.5% 'cyanos-cream' exhibits an SPF greater than 15. A 0.5% 'cyanos-cream' provides protection against UV-induced damage that is greater than commercially available sunscreen preparations purported to exhibit an SPF value of 15. Other systems and methods for determining the sunscreen activity of a compound are taught, for example in U.S. Pat. No. 5,691,158.

In addition, when we apply the commercial cream to the polystyrene culture flasks container holding the cyanobacteria during exposure to UV radiation, the polystyrene becomes translucent. This reaction does not occur unless the container is exposed to UV radiation. A photochemical reaction induces free radicals in the commercial formulations which subsequently react with the polystyrene. The commercial creams do not have sufficient protection from free radicals induced by exposure to UV radiation. This reaction does not occur with the creams of the invention. The carotenoids present in the formulations of invention quench any free radicals produced by the UV radiation. The carotenoids will also quench similar free radicals produced by UV light on skin.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications, patents and patent applications including Canadian patent application no. 2,251,457 ("Composition Including Naturally Occuring compunds from Plants, Algae and Cyanobacteria for Protectiton Against Solar Radiation.") are incorporated by reference in their entirety to the same extent as if each individual publication, patent or patent application was specifically and individually indicated to be incorporated by reference in its entirety.

We claim:

1. A sunscreen composition comprising;
   a) a carotenoid or a carotenoid derivative having sunscreen activity;
   b) a polyphenolic compound or a polyphenolic compound derivative having sunscreen activity;
   c) a light absorbing amino acid having sunscreen activity or a light absorbing amino acid derivative having sunscreen a activity; and
   d) a carrier.

2. The composition of claim 1, wherein the carotenoid comprises a cyanobacterial carotenoid.

3. The composition of claim 2, wherein the carotenoid comprises a compound selected from the group consisting of β carotene, lutein, neoxanthin, zeaxanthin, violaxanthin antheraxanthin, caloxanthin, nostoxanthin, echinenone, canthaxanthin, oscillaxanthin and myxoxanthophyll.

4. The composition of claim 1, wherein the polyphenolic compound comprises a cyanobacterial polyphenolic compound.

5. The composition of claim 4, wherein the polyphenolic compound comprises scytonemin.

6. The composition of claim 1, wherein the amino acid comprises a mycosporine amino acid.

7. The composition of claim 6, wherein the mycosporine amino acid comprises a compound selected from the group consisting of mycosporine-glycine, palythine, asterina-330, palythinol, palythene, porphyra-334, mycosporineglycine:valine and shinorine.

8. The sunscreen composition of claim 1, further comprising at least one cosmetically acceptable adjuvant or additive.

9. A sunscreen composition comprising a carrier and an effective amount of a heteroautotrophic cell extract or a photoautotrophic cell extract, the extract having sunscreen activity, the cells having been cultured under conditions of high excitation pressure.

10. The composition of claim 1 wherein the carrier is at least one of either water, a gas, a water-based liquid, an oil, a gel, an emulsion, a dispersion or a mixture thereof.

11. A personal care product comprising the composition of claim 1.

12. A method for protecting the human skin, human hair or another surface from solar radiation, comprising topically applying thereto an effective amount of the sunscreen composition of claim 1.

13. The composition of claim 1, wherein the amino acid or amino acid derivative is selected from the group consisting of tyrosine, tryptophan, a tyrosine derivative having sunscreen activity and a tryptophan derivative having sunscreen activity.

14. The composition of claim 1, wherein the carrier comprises water, a gas, a water-based liquid, an oil, a gel, an emulsion, an oil-in-water emulsion, a water in-in-oil emulsion, a dispersion or a mixture thereof.

15. The composition of claim 8, wherein the adjuvant or additive comprises a preservative, an organic solvent, a browning agent, an antioxidant, a stabilizer, an emollient, silicone, an alpha-hydroxy acid, a demulcent, an antifoaming agent, a moisturizing agent, a vitamin, a fragrance, an ionic thickener, a non-ionic thickener, a surfactant, a filler, a thickener, a sequestrant, a polymer, a propellant, an alkalinising agent, an acidifying agent, an opacifier, a fatty compound or a colorant.

16. The composition of claim 9, wherein the extract comprises:
 a) a carotenoid or a carotenoid derivative having sunscreen activity;
 b) a polyphenolic compound or a polyphenolic compound derivative having sunscreen activity;
 c) a light absorbing amino acid having sunscreen activity or a light absorbing amino acid derivative having sunscreen activity; and
 d) a carrier.

17. The composition of claim 16, comprising a carotenoid, the polyphenolic compound comprising scytonemin and the amino acid comprising a mycosporine amino acid.

18. The composition of claim 9, wherein the extract is present in an amount selected from the group consisting of 0.1% to 25% by weight and 0.1% to 10% by weight.

19. The composition of claim 9, comprising a photoautotrophic cell extract from photoautotrophic bacteria, photoautotrophic plants or photoautotrophic fungi.

20. The composition of claim 19, wherein the photoautotrophic cell extract comprises an extract from cyanobacteria.

21. The composition of claim 9, wherein the photoautotrophic cell extract comprises a cyanobacterial extract comprising myxoxanthophyll, scytonemin and mycosporine amino acid.

22. The composition of claim 9, wherein the photoautotrophic cell extract comprises a cyanobacterial extract and the conditions of high excitation pressure comprise i) about 15° C. and a light intensity of about 150 $\mu$mol $m^{-2}s^{-1}$ or ii) out 29° C. and a light intensity of about 750 $\mu$mol $m^{-2}s^{-1}$.

23. A method for protecting human skin, human hair or another surface from solar radiation, comprising topically applying thereto an effective amount of the composition of claim 9.

24. The composition of claim 1, wherein the carrier comprises a lotion or a cream.

25. The composition of claim 9, wherein the conditions of high excitation comprise culturing the photoautophic cell in a culture comprising nutrients and reactants.

26. The composition of claim 9, wherein the conditions of high excitation comprise exposing the photoautotrophic bacteria to a growth temperature comprising about an optimum growth temperature and a growth irradiance comprising about an optimum growth irradiance.

* * * * *